United States Patent
Tiegs et al.

(10) Patent No.: US 8,406,843 B2
(45) Date of Patent: Mar. 26, 2013

(54) ECG MONITORING ELECTRODE

(75) Inventors: Mark Tiegs, West Allis, WI (US);
Edward Arndt, Brookfield, WI (US)

(73) Assignee: Mark Tiegs, West Allis, WI (US)

( * ) Notice: Subject to any disclaimer, the term of this patent is extended or adjusted under 35 U.S.C. 154(b) by 718 days.

(21) Appl. No.: 12/384,375

(22) Filed: Apr. 3, 2009

(65) Prior Publication Data

US 2009/0253975 A1   Oct. 8, 2009

Related U.S. Application Data

(60) Provisional application No. 61/123,095, filed on Apr. 4, 2008.

(51) Int. Cl.
*A61B 5/0408* (2006.01)
*A61B 5/0416* (2006.01)
(52) U.S. Cl. .......................... 600/391; 600/392; 600/394
(58) Field of Classification Search .................. 600/391, 600/392, 394; 607/152
See application file for complete search history.

(56) References Cited

U.S. PATENT DOCUMENTS

| | | | |
|---|---|---|---|
| 4,274,419 A | 6/1981 | Tam et al. | |
| 4,311,152 A * | 1/1982 | Modes et al. | 600/392 |
| 4,617,935 A | 10/1986 | Cartmell et al. | |
| 5,261,402 A * | 11/1993 | DiSabito | 600/392 |
| 5,305,746 A | 4/1994 | Fendrock | |
| 5,458,141 A | 10/1995 | Neil | |
| 6,711,427 B1 | 3/2004 | Ketelhohn | |
| 7,245,957 B2 * | 7/2007 | Rowe et al. | 600/391 |

* cited by examiner

*Primary Examiner* — Lee S Cohen
(74) *Attorney, Agent, or Firm* — Peter V Machi & Associates; Peter V. Machi; Ethel R. Machi

(57) ABSTRACT

A self-prepping ECG electrode assembly is provided. The electrode assembly includes an electrode element, an electrode stud, an abrasive member, an electrolyte gel, a cover member and a securing member. The electrode element and electrode stud are adapted to be rotatable within the electrode assembly. The electrode assembly may be used with a drive tool. The electrode assembly may be placed on the skin of a patient. The skin of the patient may be prepped for an ECG by inserting the drive tool into a bore formed in the electrode stud and turning the drive tool to achieve an oscillating rotation. In this manner the abrasive pad preps the patient's skin for the ECG procedure.

18 Claims, 3 Drawing Sheets

ECG MONITORING ELECTRODE

RELATED APPLICATIONS

This application claims the benefit of U.S. Provisional Patent Application Ser. No. 61/123,095, filed 4 Apr. 2008 and entitled "ECG Monitoring Electrode"

BACKGROUND OF THE INVENTION

This invention related to an improved medical electrode which provides the capability to manually abrade the epidermal layer of the skin in contact with the electrode.

Disposable electrodes applied to the skin of a patient are used to monitor the electrical activity of bodily functions. Electrocardiogram or ECG electrodes are positioned on a patient's body to gather biopotential electrical signals generated by the heart. These signals are generally transmitted to a monitor that produces a visual representation of the patient's heart condition.

The strength and accuracy of the signals from the ECG electrodes to the monitor is dependent on motion artifacts caused by the movement of the patient's skin relative to the electrode. This movement can cause extraneous signals, shifting the desired signal baseline.

Abrading the skin reduces the electrical potential and minimizes the impedance of the patient's skin, thereby reducing motion artifacts and improving the biopotential electrical signal.

Typically, the patient's skin is prepared prior to applying the electrode. Preparatory abrasion removes a portion of the epidermis or external skin layer and is usually performed by rubbing the patient's skin with a rough surfaced material followed by cleaning the abraded area with alcohol. If the electrical potential of one or more electrodes is too great and the signal is not adequate, the electrode(s) must be removed, the site(s) further abraded, and the electrode(s) reapplied. This procedure is not only time consuming, but may be painful to the patient. The processes may also cause emotional distress to the patient as the patient views the skin abrading procedure.

SUMMARY OF THE INVENTION

The present invention provides methods and apparatus for providing and using an electrode assembly having an integrated skin abrading member.

In one embodiment the apparatus includes an electrode stud having a first end and a second end, an electrode element having a first surface and a second surface, the first surface coupled to the first end of the electrode stud and a securing element having an first surface and an opposed second surface, the securing element having a first aperture therethrough, the first aperture extending from the first surface to the second surface. The apparatus further including a snap-cover with a second aperture therethrough, the snap-cover coupled to the second surface of the electrode element. The apparatus having the electrode stud extending through the securing element first aperture and the snap-cover second aperture and rotatably retained within the second aperture.

The apparatus may include a groove formed around the electrode stud diameter, the groove being sized and configured to engage an edge of the snap-cover member aperture to rotatably retain the electrode stud within the snap-cover member aperture.

The apparatus may include the abrading means being an abrasive surface integrally formed on the second surface of the electrode element.

The apparatus may include the abrading means being an abrasive pad coupled to the second surface of the electrode element.

The securing element of the apparatus may include an adhesive on the second surface thereof.

At least a portion of the abrasive pad of the apparatus may extend below the second surface of the securing member.

The apparatus may include an electrolyte gel applied to the abrasive pad.

The abrasive pad of the apparatus may be generally disc shaped.

The electrode element and the electrode stud of the apparatus may be integrally formed.

The apparatus may include a snap-cover sized and configured to engage the electrode stud.

The apparatus may include a backing member coupled to the second surface of the securing member.

The apparatus may include a cavity formed in the backing member, the cavity being sized and configured to receive the abrasive pad.

Another aspect of the invention provides a method including providing an electrode having a securing element having a first surface and an opposed second surface, the securing element having a first aperture therethrough, the first aperture extending from the first surface to the second surface, a snap-cover having a first surface and a second surface, at least a portion of the first surface being coupled to the second surface of the securing element, the snap-cover having a second aperture therethrough, an electrode stud having a first end and a second end, the first end of the electrode stud being rotatably retained within the snap-cover aperture, an electrode element having a first surface and a second surface, the first surface being coupled to the second end of the electrode stud, abrading means coupled to the second surface of the electrode element, wherein the second surface of the securing member is covered in an adhesive material, and a backing member is removably secured to the second surface of the securing member. The method further including removing the electrode from the backing member, placing the electrode on the skin of a patient, rotating the electrode stud in a first direction and a second opposite direction to abrade the skin, and connecting a monitoring device to the electrode.

The rotating step of the method may include providing an electrode with a bore formed in the first end of the electrode stud, providing a drive tool, the drive tool having a first end sized and configured to matingly engage the electrode stud bore, inserting the drive tool into the electrode stud bore, and rotating the tool in a first direction and a second opposite direction.

The rotating step may include providing an electrode with an electrode stud having an external multi-faceted configuration, providing a drive tool, the drive tool having a first end with a bore sized and configured to matingly engage the electrode stud external configuration, placing the drive tool over the electrode stud such that the first end of the electrode stud is inserted in the drive tool bore, and rotating the tool in a first direction and a second opposite direction. In the preferred embodiment, the drive tool is hand-operated which avoids the cost, size and power consuming characteristics inherent in mechanical drive tools.

The connecting step may include providing a lead wire having a first end and a second end, connecting the first end of the lead wire to the electrode and connecting the second end of the lead wire to the monitoring device.

The connecting the first end step may include providing an alligator clip coupled to the first end of the lead wire and placing the alligator clip on the electrode stud.

Another aspect of the invention is a kit including a plurality of electrodes carried on a backing member, each electrode including a securing element having a first surface and an opposed second surface, the securing element having a first aperture therethrough, the first aperture extending from the first surface to the second surface, a snap-cover having a first surface and a second surface, at least a portion of the first surface being coupled to the second surface of the securing element, the snap-cover having a second aperture therethrough, an electrode stud having a first end and a second end, the first end of the electrode stud being rotatably retained within the snap-cover aperture, an electrode element having a first surface and a second surface, the first surface being coupled to the second end of the electrode stud, and abrading means coupled to the second surface of the electrode element. The kit further including a drive tool having a first end sized and configured to engage the first end of the electrode stud. In the preferred embodiment, the drive tool is hand-operated which avoids the cost, size and power consuming characteristics inherent in mechanical drive tools.

The kit may include an the electrode stud first end including a bore formed therein and the drive tool having an exterior configuration sized and configured to engage the interior of the electrode stud bore.

The kit may further include the drive tool having a bore formed in the first end thereof, the bore being sized and configured to engage the first end of the electrode stud.

BRIEF DESCRIPTION OF THE DRAWINGS

FIG. 4 shows the electrode assembly during abrasion while FIGS. 5A and 5B show the electrode assembly during monitoring using various lead wire connectors.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
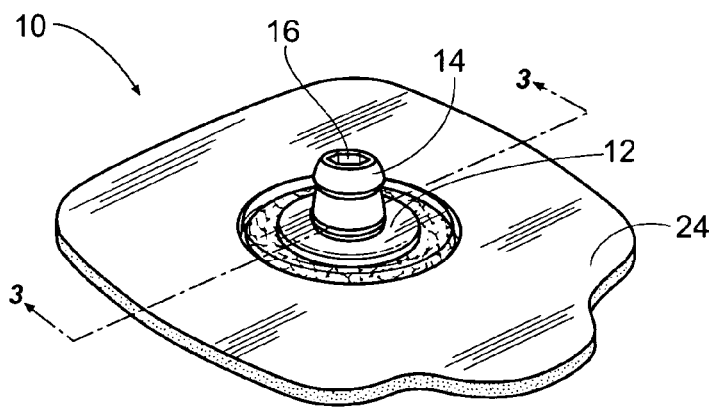
FIG. 1 is a perspective view of an embodiment of an electrode assembly according to the present invention.
Figure 2:
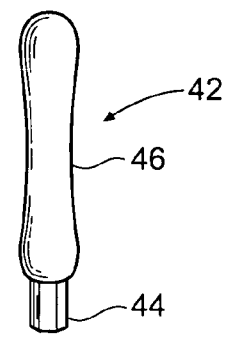
FIG. 2 is an exploded view of the electrode assembly of FIG. 1 including a drive tool.
Figure 2:
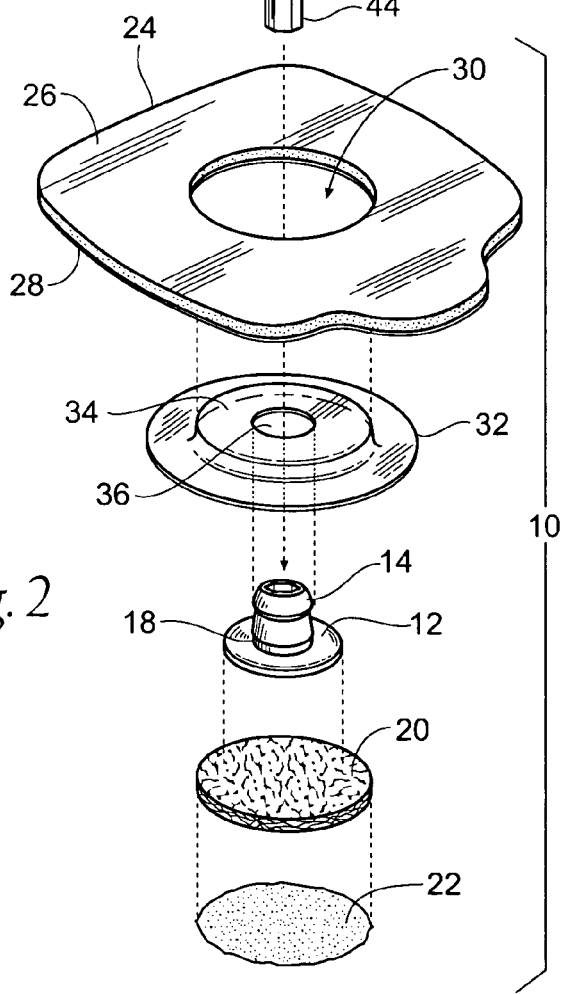

FIG. 1 shows an electrode assembly 10 according to the present invention. As shown in FIG. 2, the electrode assembly preferably includes a securing element 24, a snap-cover member 32, an electrode stud 14, and electrode element 12, an abrasive pad 20, and an electrolyte gel 22.

As shown in FIG. 1 the electrode assembly 10 preferably includes an electrode element 12 coupled to an electrode stud 14. In the preferred embodiment the electrode element 12 and the electrode stud 14 are integrally formed. However, it is contemplated that these elements 12, 14 could be formed separately and coupled by any means known in the art. The electrode element 12 may be of any type known in the art, including but not limited to silver/silver chloride plated, 20% glass-filled ABS. The electrode stud 14 is typically made from the same material as the electrode element 12. The electrode element may optionally be covered with a sheath (not shown). The sheath may be made from various metals such as, but not limited to, stainless steel or nickel plated brass.

Figure 5A:
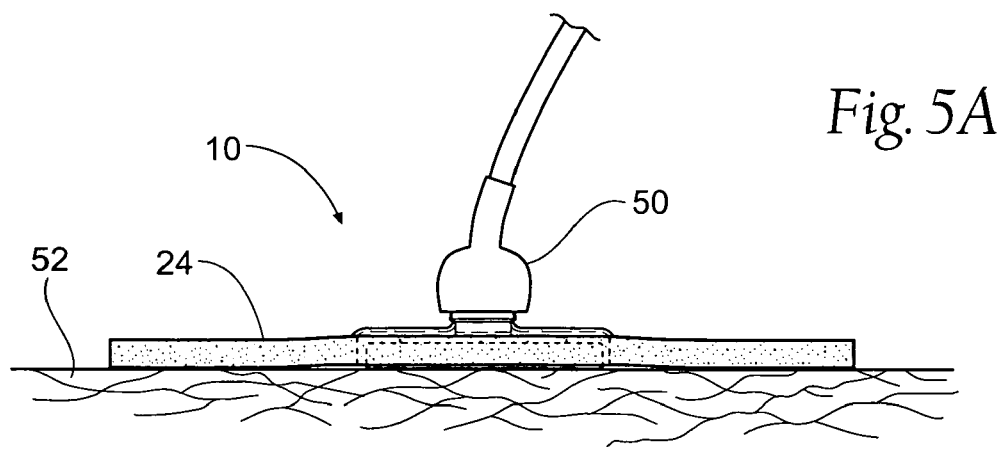
Figure 5B:
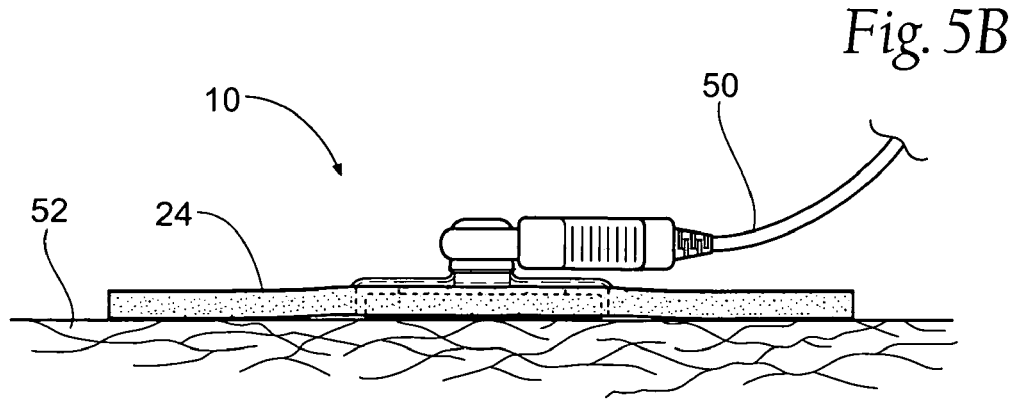

The electrode stud 14 is sized and configured to make an electrical connection with the lead wires of a monitoring apparatus 50 as shown in FIG. 5. The current industry standard is to utilize a snap fit between an electrode and the lead wires of a monitoring apparatus 50. The illustrated embodiment shows an electrode element 10 adapted to mate with current industry standard lead wires. However, it is contemplated that the particular external configuration of the electrode stud 14 may be altered based on the particular monitoring apparatus 50 it is to be used with. In this manner the electrode stud 14 external configuration may be altered such that it mates with the lead wire of any particular monitor 50.

Figure 3:
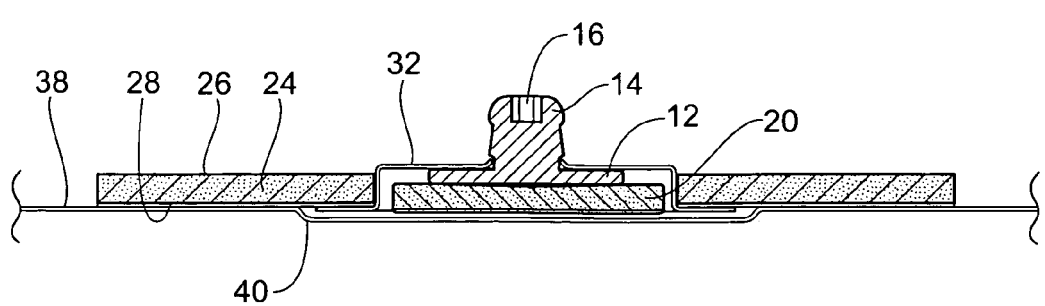
FIG. 3 is a cross sectional view of an electrode assembly taken along line 3-3 of FIG. 1.

It is further contemplated that the electrode stud 14 may be formed with a groove 18 extending around its diameter as shown in FIG. 2. This groove 18 may be used to retain the snap-cover 32 as shown in FIG. 3. The groove 18 may form a lip sealing surface with the snap-cover 32 to seal the gel 22 between the snap-cover member 32 and the backing member 38. In this manner, the gel is prevented from migrating outward towards the free end of the stud 14 and connection cable 50.

The electrode stud 14 preferably includes a bore 16. As shown in FIGS. 1 and 3, the bore 16 preferably extends through at least a portion of the electrode stud 14, along the axis thereof. The bore 16 is sized and configured to mate with a tool 42, as will be described below. In the illustrated embodiment the bore 16 has a hexagonal cross section, however it is contemplated that alternative cross sections could be utilized, including but not limited to rectangular, square, triangular, x-shaped and star-shaped. The bore 16 may take any shape which allows a mating tool 42 to be inserted into the bore 16 and engage the bore 16 such that as the tool 42 is rotated the electrode stud 14 is also rotated.

The electrode assembly 10 preferably includes an abrasive pad 20 coupled to the electrode element 12, as shown in FIG. 3. The abrasive pad 20 is preferably sized to be at least as large as the electrode element 12. In this manner, all surfaces of the skin beneath the electrode element 12 will be abraded. It may be desirable for the abrasive pad 20 to be slightly larger than the electrode element 12 as shown in FIG. 3. The abrasive pad 20 may be made of any material known in the art. Preferably the abrasive pad 20 is flexible to allow the pad to confirm to the contour of the patient's skin.

It is contemplated that different patients may require different types of skin preparation. For this reason the abrasiveness of the pad 20 may be varied based on patient needs. In this manner, different abrasive pads 20 may have a different level of abrasiveness to be used in different patient situations. Various electrode elements may be manufactured with various levels of abrasiveness. The electrode element 10 with the desired level of abrasiveness of the abrasive pad 20 may be chosen by the medical provider.

Although the illustrated embodiment shows an abrasive pad 20 that is separate from the electrode element 12, it is contemplated that the electrode element 12 itself could be provided with an abrasive surface. It is contemplated that this abrasive surface could be molded into the electrode element 12 or could be a treatment applied to the surface of the electrode element 12.

The electrode assembly 10 preferably includes an electrolyte gel 22 carried by the abrasive pad 20. The electrolyte gel 22 is utilized to decrease impedance between the skin and the electrode. The electrolyte gel 22 may be of any type known in the art. The electrolyte gel 22 is preferably a liquid gel which is saturated into the abrasive pad 20.

Figure 4:
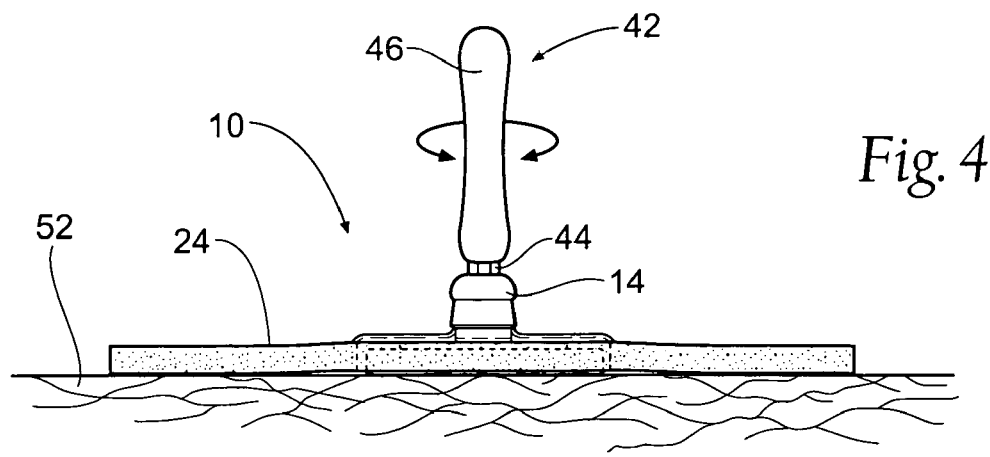
FIGS. 4, 5A and 5B are side views of the electrode assembly of FIG. 1 applied to the skin of a patient.

The electrode assembly 10 preferably includes a securing element 24. The securing element 24 secures the electrode assembly 10 to the skin 52 of the patient as shown in FIGS. 4 and 5. In the illustrated embodiment the securing element 24 comprises a flexible member. The securing element 24 has an exterior side 26 and an interior side 28 which contact the skin 52. The interior side 28 is preferably treated with an adhesive to removably adhere the electrode assembly 10 to the skin 52 of the patient. Although the illustrated embodiment the securing element 24 is made of a foam material, it is contemplated that any material known in the art may be utilized.

The securing element 24 preferably includes an aperture 30 therethrough, as shown in FIG. 2. The electrode element 10 is preferably disposed generally within the aperture 30. Although the illustrated embodiment has a circular aperture 30, the aperture 30 may be of any shape sized and configured to allow the electrode 12 to rotate freely within the aperture 30.

The electrode assembly 10 preferably includes a snap-cover member 32. The snap-cover member 32 preferably includes an aperture 36 therein through which the electrode stud 14 may extend, as shown in FIG. 3. The snap-cover member 32 may be secured to the interior side 28 of the securing element 24. It is further contemplated that the edge of the aperture 36 may he shaped in an hour-glass form to create a lip seal with the groove 18 in the electrode stud 14. In the illustrated embodiment the snap-cover member 32 includes a raised portion 34 that forms a cavity. Preferably the snap-cover member 32 is slightly larger than aperture 30 in securing element 24 so as to snap-cover the aperture 30 as shown in FIG. 3. The snap-cover member 32 may be secured to the electrode stud 14 by snapping into groove 18 formed in the electrode stud 14. The electrode assembly is preferably carried on a backing member 38. The backing member 38 may be formed with a cavity 40 as shown in FIG. 3. The cavity 40 is preferably sized and configured to receive the abrasive pad 20.

Figure 6:
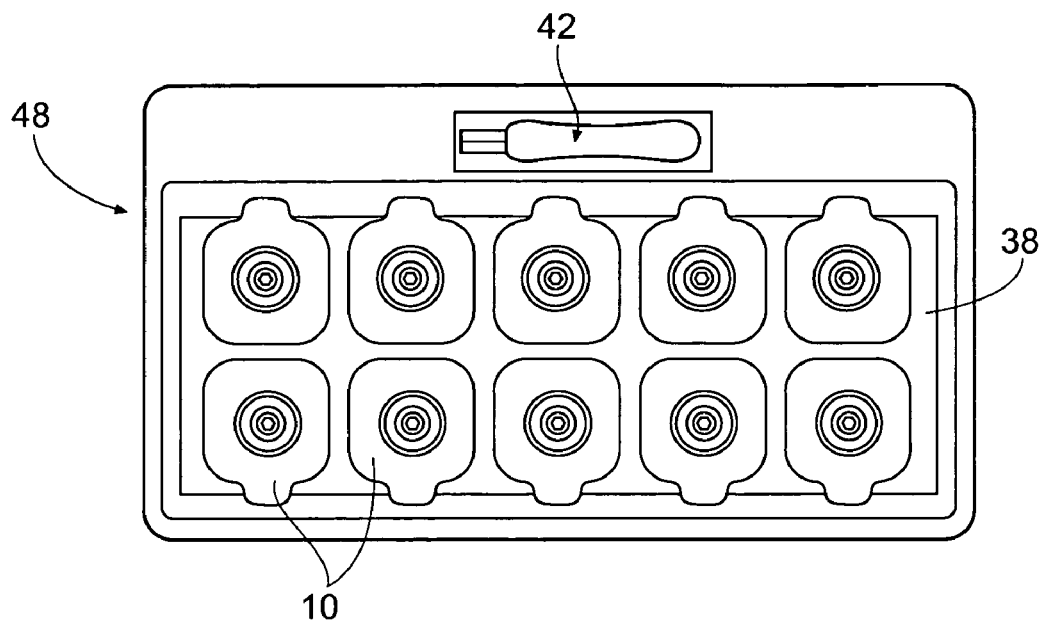
FIG. 6 is a top view of a kit including an electrode assembly and drive tool according to the present invention.

It is contemplated that multiple electrode assemblies 10 may be carried on a single backing member 38 as shown in FIG. 6. An ECG procedure generally uses 10 electrodes so it may be desirable to package 10 electrode assemblies 10 on a single backing member 38 as shown in the illustrated embodiment. However, it is contemplated that any number of electrode assemblies 10 may be carried on a single backing member 38.

FIG. 2 shows a tool 42 sized and configured to be used with the electrode assembly 10 of the present invention. The tool 42 preferably includes a head portion 44 and a handle 46. In the illustrated embodiment the head portion 44 and the handle portion 46 are integrally formed. However it is also contemplated that the head portion 44 and the handle portion 46 may be formed separately and coupled using any means known in the art. The head portion 44 is sized and configured to mate with the bore 16 formed in the electrode stud, as shown in FIG. 4. In the illustrated embodiment the head portion 44 has a generally hexagonal cross section, however it is contemplated that the head portion 44 may take various other cross sections to correspond with the shape of the electrode stud bore 16.

Figure 7:
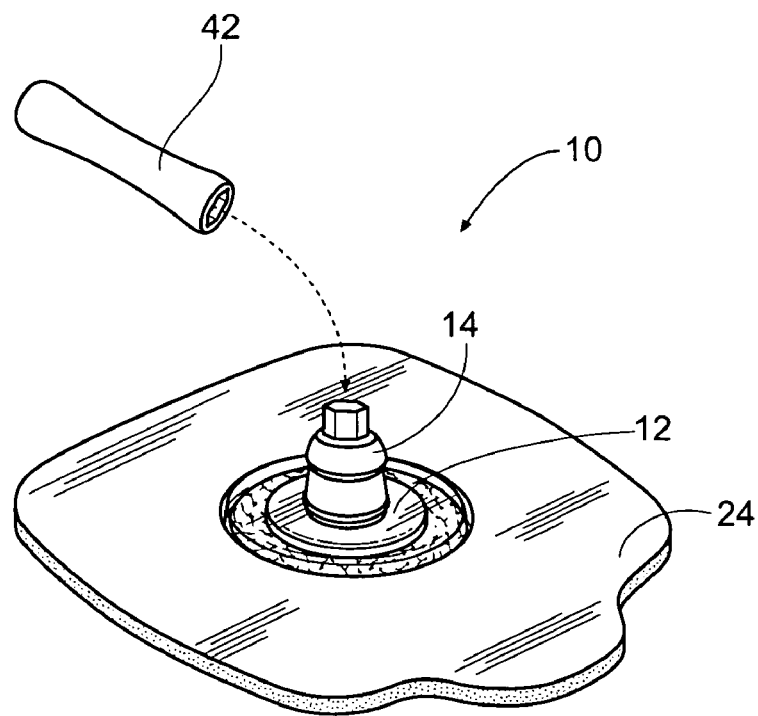
FIG. 7 is a perspective view of an alternative embodiment of an electrode assembly.

It is also contemplated that as shown in FIG. 7, the stud 14 or snap-cover (not shown) to be used with the stud 14 could be formed with an external multi-faceted configuration, rather than an interior bore 16. In such an embodiment, the drive tool 42 would have a mating internal multi-faceted configuration. In such an embodiment the external multi-faceted configuration of the stud 14 would preferably be adapted to engage the connection cable 50.

In use, at least one electrode assembly 10 may be provided in a sealed package 48 with at least one drive tool 42 as shown in FIG. 6. Preferably, an appropriate number of electrode assemblies 10 to perform a single ECG are packed together. The medical provider may open the package 48 and peel a first electrode assembly 10 from the backing member 38. The electrode assembly 10 is then placed on a predetermined location on the skin 52 of the patient. The medical provider may then insert the head 44 of the drive tool 42 into the bore 16 formed in the electrode stud 14. The tool 44 may be turned by its handle 46 to abrade the skin 52. Preferably, the motion is an oscillating rotation, and will be turned at least one time in both the clockwise and counterclockwise direction. However it is contemplated that the handle may be turned in a single direction. It is further contemplated that the handle does not need to make a complete rotation in either direction.

In this manner, the patient's skin does not have to be prepped, whether by an abrasive pad or abrasive gel or lotion, prior to applying the electrode assembly 10. The abrasion provided by the abrasive pad 20 along with the electrolyte gel 22 will reduce the impedance between the patient's skin 52 and the electrode element 12 such that the ECG procedure may be performed. If the impedance remains too high, the medical care provider may simply reinsert the drive tool 42 into the electrode stud bore 16 and further abrade the skin 52.

The medical provider may place all of the electrode assemblies 10 on the skin 52 of the patient, and then perform the skin abrasion procedure for each electrode assembly 10. Alternatively, the medical provider may perform the skin abrasion procedure for each electrode assembly 10 as the electrode assembly 10 is secured to the skin 52 of the patient.

In use, the abrasive pad 20 provides volumetric space to encapsulate the electrolyte gel 22. The slight downward pressure and oscillating rotation from the tool evenly distributes the electrolyte gel 22 and disperses any bubbles which may cause impedance. The motion of the abrasive pad 20 causes the electrolyte gel 22 to wet the skin and emulsifies the electrolyte gel 22 to create a conductive path between the patient's skin 52 and the electrode element 12. Many typical electrodes require a waiting period of up to 15 minutes of "settling time" to obtain a good connection between the patient's skin and the electrode. The present invention eliminates that settling time.

It is contemplated that the multiple electrode assemblies 10 could be provided in a kit along with a tool 42. The multiple electrode assemblies 10 may be provided on a single backing member 38. The kit may further be provided with any other item that may be useful for positioning the electrodes 10 including, but not limited to alcohol pads.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

We claim:

1. An apparatus comprising:
   an electrode stud, the electrode stud having a first end, a second end and a diameter;
   an electrode element, the electrode element having a first surface and a second surface, the first surface being coupled to the first end of the electrode stud;
   a securing element, the securing element having an first surface and an opposed second surface, the securing element having a first aperture therethrough, the first aperture extending from first surface to the second surface;
   a groove, formed around the electrode stud diameter;
   a snap-cover, the snap-cover being coupled to the second surface of the securing element, the snap-cover having a second aperture therethrough;
   the second aperture of the snap-cover defining an edge wherein the edge is configured to engage the groove to effect the electrode stud being rotatably retained within the second aperture;
   abrading means coupled to the second surface of the electrode element for abrading the surface of the skin of the patient and contouring to the surface of the skin of the patient so as to maximize conductive surface contact with the skin and simultaneously prevent movement of the electrode element and said abrading means except on application of a sufficient amount of force to the electrode element; and
   wherein the electrode stud extends through the securing element first aperture and the snap-cover second aperture and is rotatably retained within the second aperture.

2. The apparatus of claim 1 wherein the edge is further sized and configured to engage the groove to prevent electrolyte gel from migrating outward towards the second end of the electrode.

3. The apparatus of claim 1 wherein the abrading means further comprises an abrasive surface integrally formed on the second surface of the electrode element.

4. The apparatus of claim 1 wherein the abrading means further comprises an abrasive pad coupled to the second surface of the electrode element.

5. The apparatus of claim 4 wherein at least a portion of the abrasive pad extends below the second surface of the securing member element.

6. The apparatus of claim 5 further comprising a backing member coupled to the second surface of the securing member element.

7. The apparatus of claim 6 further comprising a cavity formed in the backing member, the cavity being sized and configured to receive the abrasive pad.

8. The apparatus of claim 4 further comprising an electrolyte gel applied to the abrasive pad.

9. The apparatus of claim 4 wherein the abrasive pad is generally disc shaped.

10. The apparatus of claim 1 wherein the securing element includes an adhesive on the second surface thereof.

11. The apparatus of claim 1 wherein the electrode element and electrode stud are integrally formed.

12. A method comprising:
    providing an electrode, the electrode having:
    a securing element, the securing element having a first surface and an opposed second surface, the securing element having a first aperture therethrough, the first aperture extending from the first surface to the second surface;
    a snap-cover, the snap-cover having a first surface and a second surface, at least a portion of the first surface being coupled to the second surface of the securing element, the snap-cover having a second aperture therethrough;
    an electrode stud having a first end and a second end, the electrode stud being rotatably retrained within the snap-cover aperture,
    an electrode element having a first surface and a second surface, the first surface being coupled to the second end of the electrode stud,
    abrading means coupled to the second surface of the electrode element,
    wherein the second surface of the securing element is covered in an adhesive material, and
    a backing member is removably secured to the second surface of the securing element;
    removing the backing member from the second surface of the securing element;
    placing the electrode on the skin of a patient;
    rotating the electrode stud in a first direction and a second opposite direction to abrade the skin; and
    connecting a monitoring device to the electrode.

13. The method of claim 12 wherein the rotating step further comprises:
    providing the electrode with a bore formed in the first end of the electrode stud;
    providing a drive tool, the drive tool having a first end sized and configured to matingly engage the electrode stud bore;
    inserting the drive tool into the electrode stud bore;
    rotating the tool in a first direction and a second opposite direction.

14. The method of claim 12 wherein the rotating step further comprises:
    providing the electrode with an electrode stud having an external multi-faceted configuration;
    providing a drive tool, the drive tool having a first end with a bore sized and configured to matingly engage the electrode stud external configuration;
    placing the drive tool over the electrode stud such that the first end of the electrode stud is inserted in the drive tool bore;
    rotating the tool in a first direction and a second opposite direction.

15. The method of claim 12 wherein the connecting step further comprises:
    providing a lead wire having a first end and a second end;
    connecting the first end of the lead wire to the electrode; and
    connecting the second end of the lead wire to the monitoring device.

16. A kit comprising:
    a plurality of electrodes carried on a backing member, each electrode including:
    a securing element, the securing element having a first surface and an opposed second surface, the securing element having a first aperture therethrough, the first aperture extending from the first surface to the second surface;
    a snap-cover, the snap-cover having a first surface and a second surface, at least a portion of the first surface being coupled to the second surface of the securing element, the snap-cover having a second aperture therethrough;
    an electrode stud having a first end and a second end, the electrode stud being rotatably retrained within the snap-cover aperture,
    an electrode element having a first surface and a second surface, the first surface being coupled to the second end of the electrode stud, and abrading means coupled to the second surface of the electrode element; and a hand-operated drive tool having a first end sized and configured to engage the first end of the electrode stud.

17. The kit of claim 16 wherein
the electrode stud first end includes a bore formed therein; and
the drive tool has an exterior configuration sized and configured to engage the interior of the electrode stud bore.

18. The kit of claim 16 wherein the drive tool has a bore formed in the first end thereof, the bore being sized and configured to engage the first end of the electrode stud.

* * * * *